United States Patent [19]

Chanayem

[11] Patent Number: 5,271,264
[45] Date of Patent: Dec. 21, 1993

[54] METHOD OF IN-SITU PARTICLE MONITORING IN VACUUM SYSTEMS

[75] Inventor: Steve G. Chanayem, Sunnyvale, Calif.

[73] Assignee: Applied Materials, Inc., Santa Clara, Calif.

[21] Appl. No.: 800,476

[22] Filed: Nov. 27, 1991

[51] Int. Cl.$^5$ .............................................. G01N 33/00
[52] U.S. Cl. .............................. 73/28.01; 250/492.2
[58] Field of Search ................ 73/28.01, 28.02, 28.03, 73/28.04, 28.05, 28.06, 24.03; 250/397, 492.2, 492.3

[56] References Cited
FOREIGN PATENT DOCUMENTS 208742 8/1988 Japan .................................. 73/28.01

Primary Examiner—Hezron E. Williams
Assistant Examiner—Joseph W. Roskos
Attorney, Agent, or Firm—Noel F. Heal

[57] ABSTRACT

Detecting the presence of particles in a vacuum chamber is effected by positioning an in-situ particle monitor downstream of a pump connected to the chamber. The downstream position of the particle monitor is contrary to the normal practice of locating the particle monitor upstream of the pump, i.e. between the pump and the chamber. The invention avoids problems associated with placing the monitor immediately adjacent to the vacuum chamber, where it is subject to errors and possible surface damage caused by the process taking place in the chamber, and where it may have a lower particle detection probability.

3 Claims, 2 Drawing Sheets

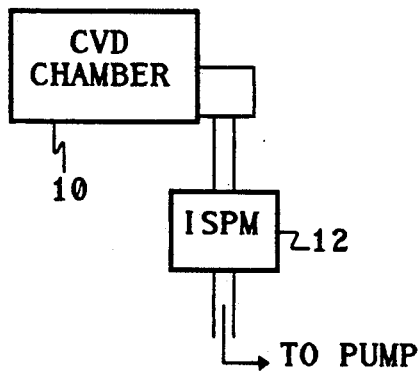
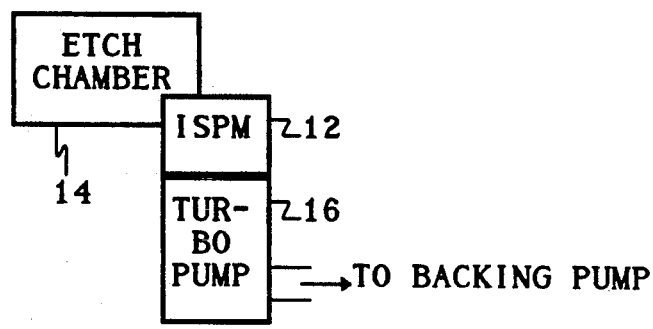
FIG. 1 (PRIOR ART)   FIG. 2 (PRIOR ART)
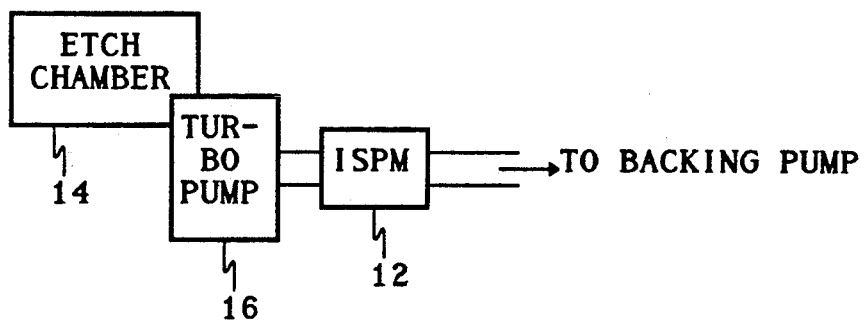
FIG. 3

METHOD OF IN-SITU PARTICLE MONITORING IN VACUUM SYSTEMS

BACKGROUND OF THE INVENTION

This invention relates generally to vacuum systems used in semiconductor processing and, more particularly, to techniques for detecting particles in, or exhausted from, a vacuum chamber. Many process steps in the fabrication of semiconductor circuits are performed in a vacuum or near-vacuum. With the continuing trend toward larger integrated circuits and smaller device geometries, even extremely small (i.e. submicron) contaminating particles present in a vacuum chamber can shadow the surface of a semiconductor wafer being processed and produce a device defect. Therefore, monitoring the presence of particles in a vacuum chamber is of critical concern to semiconductor process engineers.

The number of such particles that affect a wafer can be determined by inspection of the wafer after processing, but it is far more desirable to obtain an indication of particle level while processing is still proceeding. In-situ monitoring for particles permits process engineers to identify any trouble points in the process, and to take possible corrective action.

An example of an in-situ particle flux monitor is one made by High Yield Technology, Inc. of Sunnyvale, Calif., under the model designation PM-150. The monitor can be mounted in a load-lock, exhaust line, or vacuum chamber of an ion implantation machine. In a paper entitled "Real-Time, In-Situ Particle Monitoring in a High Current Ion Implantation Production Bay" by Weisenberger et al., Proc. of the Seventh Intl. Conf. on Ion Implantation Technology, Kyoto, Japan, Jun. 7, 1988, the use of a High Yield Technology PM-150 monitor within the end station of a Varian ion implantation machine is described.

U.S. Pat. No. 5,047,648 discloses another type of in-situ particle monitor, using a laser beam and an associated light detector to detect light scattered from particles that enter the monitor. The monitor includes an enclosure or radiation-blocking material, with an aperture to admit a stream of gas containing the particles to be detected. As a particle passes through the monitor, a beam of light from a solid-state laser within the enclosure impinges on the particle and is scattered. Part of the scattered light is focused by suitable optics onto a photodetector, which effectively detects the presence of the particle and is coupled to detection circuitry for accumulating a particle count or rate.

For some processes, a particle monitor of this type is best installed directly in a vacuum chamber. For other processes, particle contamination is best monitored immediately downstream of the vacuum chamber, in an exhaust line through which gases are withdrawn from the chamber and a vacuum is established and maintained. In some cases, particle counting in a downstream monitor becomes a complex task. For example, if the process taking place in the vacuum chamber is a plasma etch process, and a turbo pump is attached to the exhaust line, there are some significant difficulties with installing a particle monitor between the process chamber and the turbo pump. Specifically, emission of light from the plasma will cause noise and erroneous counts in the particle monitor. Further, residual active ions from the plasma will degrade sensitive surfaces of the monitor. And finally, since the turbo pump has an input port of relatively large cross-sectional area, the monitor will be able to cover only a small fraction of this cross section, which means that the probability of accurate particle detection is significantly diminished.

It will be appreciated that the placement of an in-situ particle monitor immediately downstream of a vacuum chamber, in an exhaust line, sometimes has difficulties associated with it, and that there is a need for an improved technique of in-situ particle monitoring. The present invention is directed to this end.

SUMMARY OF THE INVENTION

The present invention resides in an improved method of in-situ particle monitoring for use in vacuum processing systems. Briefly, and in general terms, the method comprises the steps of connecting a pump directly to a vacuum chamber, and connecting an in-situ particle monitor downstream of the pump, to detect particles pumped from the vacuum chamber. The particle monitor in its downstream position is less susceptible to errors and damage that may be caused by processes taking place in the vacuum chamber.

In the illustrative embodiment of the invention, the pump is a high-vacuum pump, such as a turbomolecular pump having an inlet port of relatively large cross-sectional area. Connecting the particle monitor downstream of the pump provides a larger ratio of detection cross section to flow cross section, and thereby improves the accuracy of the particle monitor. The illustrative embodiment of the invention is specifically concerned with monitoring particles in a plasma etch chamber. In this case, the method includes connecting a turbomolecular pump directly to the plasma etch vacuum chamber, and connecting an in-situ particle monitor downstream of the turbomolecular pump, to detect particles pumped from the plasma etch vacuum chamber. The particle monitor in its downstream position is less susceptible to errors caused by plasma emission, and to surface damage that may be caused by residual active ions. The particle monitor in its downstream position also has a larger ratio of detection cross section to flow cross section, and therefore has a higher probability of providing an accurate particle count.

BRIEF DESCRIPTION OF THE DRAWINGS

FIGS. 1 and 2 are fragmentary diagrammatic views of prior art vacuum processing systems in which an in-situ particle monitor (ISPM) is installed immediately downstream of a processing chamber, in an exhaust line connected to the chamber;

FIG. 3 is a fragmentary diagrammatic view of a vacuum processing system in accordance with the invention;

DESCRIPTION OF THE PREFERRED EMBODIMENT

Figure 4:
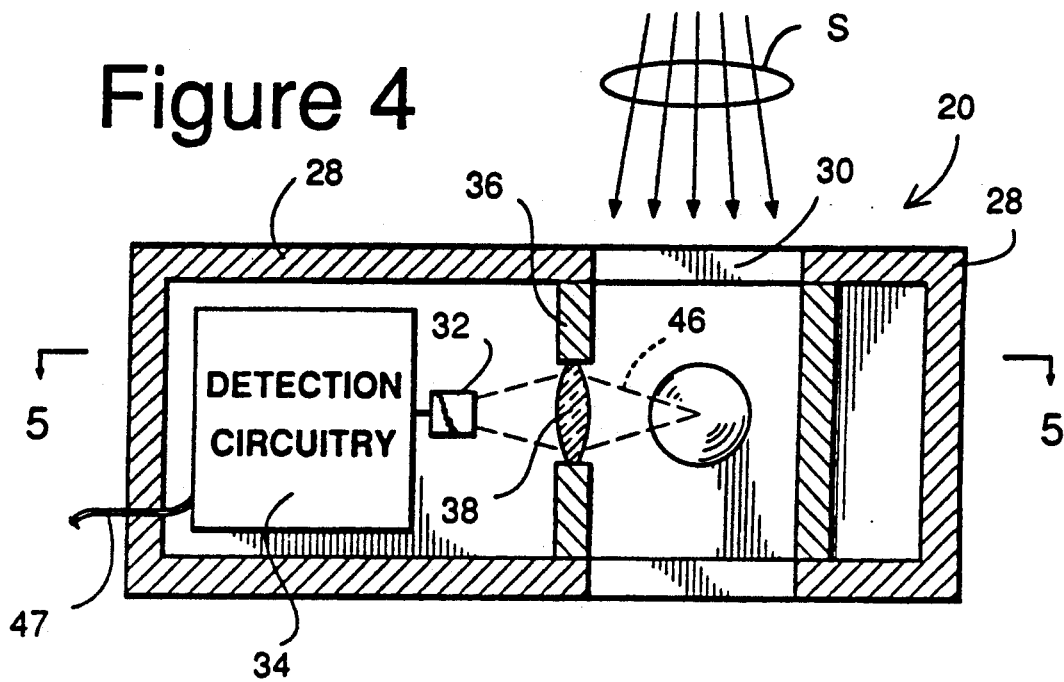
FIG. 4 is an elevational view, partly in cross section, of an in-situ particle monitor of the type used in the present invention.

As shown in the drawings for purposes of illustration, the present invention is concerned with particle monitors used to measure the number or rate of flow of particles in an exhaust line from a vacuum chamber. In many semiconductor fabrication processes, it is important for a process engineer to know the level of particulate contamination in a vacuum process chamber. A useful way to obtain this information is to position an in-situ particle monitor in the exhaust line.

FIG. 1 depicts an in-situ particle monitoring technique for measuring particle contamination in a vacuum chamber 10 used for chemical vapor deposition (CVD) processing. An in-situ particle monitor (ISPM) 12 is positioned in an exhaust line from the chamber 10, between the chamber and a vacuum pump (not shown).

FIG. 2 shows how the same technique might be applied to a plasma etching process. The ISPM 12 is positioned immediately adjacent to an etch chamber 14 and immediately upstream of a turbo pump 16, the output of which is connected to a backing pump (not shown). Plasma etching is performed in a high vacuum, and a turbo pump, or turbomolecular pump, is most often used to maintain the vacuum. By way of background, a turbo pump has multiple stages of turbine blades that rotate at high speeds (24,000–36,000 rpm.) At suitably low pressures, essentially all collisions by gas molecules are with the pump blades, thereby efficiently transferring momentum from the pump to the gas, and maintaining the desired vacuum. At higher pressures, collisions between gas molecules prevent the turbo pump from operating as efficiently, so a backing pump is required to keep the forepressure low enough to be within the efficient operating regime of the turbo pump.

It appears to be well established that the only appropriate place to locate a particle monitor in a vacuum chamber exhaust line is immediately downstream of the chamber being monitored. For example, this concept was illustrated in a series of ten papers captioned "In Situ Particle Monitoring in the 90's: The Series," recently published in Microcontamination (1991, Canon Communications, Inc.) In particular, the second paper of this series, published in February, 1991, and entitled "Installing In Situ Sensors in Single-Wafer Plasma Etchers," by Peter Borden, shows the use of particle sensors in the exhaust line from a process chamber, and in the exhaust lines from input and output load-locks. In each case, the particle sensor is located immediately downstream of the vacuum chamber being monitored.

However, the installation of a particle monitor between a plasma process chamber and a turbo pump has high-lighted a number of problems associated with this approach. Notably, the proximity of the particle monitor to the plasma process causes noise and erroneous particle counts in the monitor, and residual active ions from the plasma process can degrade sensitive surfaces of the monitor. Moreover, because a turbo pump inlet port requires a relatively large cross-sectional area, there is a small ratio of detection cross section to flow cross section, which reduces particle detection probability.

In accordance with the invention, and as shown in FIG. 3, the in-situ particle monitor 12 is placed downstream of the pump 16, and not immediately adjacent to the etch chamber 14. At first impression, this approach would seem to be counterproductive. Intuitively, it would seem that a monitor located downstream of the high-vacuum pump would tend to accumulate particles rather than count them as they streamed through. However, this assumption has proved to be unfounded. Perhaps more importantly, the difficulties associated with locating the particle monitor upstream of the pump are practically eliminated by the technique of the invention.

The only significant new problem posed by locating the particle monitor downstream of the pump is that, because the monitor is in a cooler location, there is a tendency for byproducts of the plasma process to condense on cool surfaces of the monitor. Obviously, it would be undesirable to permit this condensation on lenses and other optical components of the monitor. Fortunately, there is a simple solution to this problem: heating the affected surfaces to eliminate or minimize condensation.

Figure 5:
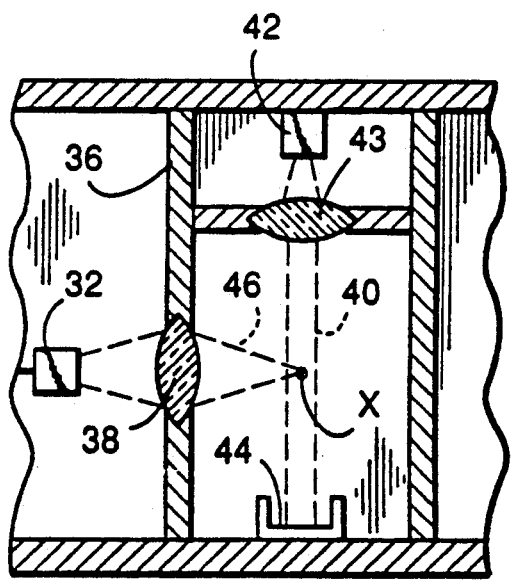
FIG. 5 is a fragmentary cross-sectional view taken generally along the line 5—5 of FIG. 4.

By way of further background, FIGS. 4 and 5 show a particle monitor of the type used in the present invention. This is the monitor disclosed in U.S. Pat. No. 5,047,648. The particle detector, referred to by numeral 20 in FIGS. 4 and 5, includes enclosure walls 28 having an aperture 30 aligned with a stream S of free particles. A photodetector 32 and detection circuitry 34 are positioned behind an opaque barrier wall 36 which only permits light to enter via optics 38. A laser beam 40 is generated by a solid state laser 42, shaped by optics 43, and is ultimately absorbed within a light trap 44. When the laser beam 40 impinges on a particle X from the stream S, some of the laser beam 40 is scattered, as illustrated at 46, and is focused by optics 38 on the photodetector 32. The detection circuitry 34 amplifies and analyzes the signal produced by the photodetector 32 and provides a digital or analog particle output signal on line 46.

It will be appreciated from the foregoing that the present invention represents a significant advance in the field of semiconductor wafer processing, or in any field involving contamination-free processing in a vacuum chamber. Specifically, by performing particle monitoring downstream of a pump connected to the vacuum chamber, the method of the invention eliminates problems associated with prior art approaches. It will be appreciated that, although the invention has been described in the context of a specific illustrative embodiment, various modifications may be made without departing from the spirit and scope of the invention. Accordingly, the invention is to be defined only by the following claims.

I claim:

1. A method for detecting particles in a vacuum chamber, comprising the steps of:
   connecting a pump directly to the vacuum chamber; and
   connecting an in-situ particle monitor downstream of the pump;
   activating the pump; and
   detecting, in the in-situ particle monitor, particles pumped from the vacuum chamber, whereby the particle monitor in its downstream position is less susceptible to errors and damage caused by processes taking place in the vacuum chamber.

2. A method as defined in claim 1, wherein:
   the pump is a high-vacuum pump, such as a turbomolecular pump having an inlet port of relatively large cross-sectional area, whereby connecting the particle monitor downstream of the pump provides a larger ratio of detection cross section to flow cross section, and thereby improves the accuracy of the particle monitor.

3. A method for detecting particles in a plasma etch vacuum chamber, comprising the steps of:
   connecting a turbomolecular pump directly to the plasma etch vacuum chamber; and
   connecting an in-situ particle monitor downstream of the turbomolecular pump;
   activating the turbomolecular pump; and detecting particles pumped from the plasma etch vacuum chamber, whereby the particle monitor in its downstream position is less susceptible to errors caused by plasma emission, and to surface damage caused by residual active ions, and whereby the particle monitor in its downstream position has a larger ratio of detection cross section to flow cross section.

* * * * *